(12) United States Patent
Yamauchi

(10) Patent No.: US 7,546,758 B2
(45) Date of Patent: Jun. 16, 2009

(54) ANTI-CORROSION STRUCTURE OF GAS SENSOR

(75) Inventor: Masanobu Yamauchi, Aichi-ken (JP)

(73) Assignee: Denso Corporation, Kariya (JP)

( * ) Notice: Subject to any disclaimer, the term of this patent is extended or adjusted under 35 U.S.C. 154(b) by 131 days.

(21) Appl. No.: 11/727,058

(22) Filed: Mar. 23, 2007

(65) Prior Publication Data

US 2007/0227228 A1    Oct. 4, 2007

(30) Foreign Application Priority Data

Mar. 31, 2006   (JP)   ............................. 2006-099193

(51) Int. Cl.
  *G01N 7/00*   (2006.01)
(52) U.S. Cl. ....................... 73/31.05; 73/23.2; 73/23.31
(58) Field of Classification Search ................ 73/23.2, 73/23.31, 31.05; 204/424, 426, 427, 428, 204/431
See application file for complete search history.

(56) References Cited

U.S. PATENT DOCUMENTS

| | | | | |
|---|---|---|---|---|
| 5,238,552 A | * | 8/1993 | Kato et al. | .................. 204/428 |
| 2003/0150254 A1 | * | 8/2003 | Fujita et al. | ................... 73/23.2 |
| 2005/0241937 A1 | * | 11/2005 | Shichida et al. | ............. 204/424 |

FOREIGN PATENT DOCUMENTS

JP    10-010082    1/1998

* cited by examiner

*Primary Examiner*—Daniel S Larkin
(74) *Attorney, Agent, or Firm*—Nixon & Vanderhye, PC

(57) ABSTRACT

An anti-corrosion structure of a gas sensor is provided. The gas sensor includes a hollow cylindrical air cover assembly made up of an inner and an outer cover. The air cover assembly has formed therein air inlets through which air is admitted into the gas sensor. The inner and outer covers are joined together through at least one crimped portion which defines a water drain path extending from the air inlets to outside the air cover assembly, thereby draining the water entering at the air inlets out of the gas sensor. This avoids accumulation of the water between the inner and outer covers to minimize gap corrosion therebetween.

3 Claims, 9 Drawing Sheets

ANTI-CORROSION STRUCTURE OF GAS SENSOR

CROSS REFERENCE TO RELATED DOCUMENT

The present application claims the benefit of Japanese Patent Application No. 2006-99193 filed on Mar. 31, 2006, the disclosures of which are incorporated herein by reference.

BACKGROUND OF THE INVENTION

1. Technical Field of the Invention

The present invention relates generally to a gas sensor which may be employed in measuring the concentration of a selected component of exhaust gasses emitted from automotive engines, and more particularly to an anti-corrosion structure of such a gas sensor.

2. Background Art

Japanese Patent First Publication No. 10-10082 discloses a gas sensor to be installed in an exhaust pipe of an internal combustion engine for automotive vehicles to measure the concentration of a given gas component of exhaust emissions. FIG. 8 shows such a type of a gas sensor 9.

The gas sensor 9 consists essentially of a sensor element (not shown) to measure the concentration of a gas (will also be referred to below as a measurement gas), a housing (not shown) in which the sensor element is retained, and an air cover assembly 94 joined to a base end of the housing.

The air cover assembly 94 is, as illustrated in FIGS. 8 and 9, made up of an inner cover 941 and an outer cover 942. The inner cover 941 is joined to the base end of the housing. The outer cover 942 surrounds a base end portion (i.e., an upper end portion, as viewed in the drawings) of the inner cover 941.

The inner cover 941 and the outer cover 942 have portions 943 crimped circumferentially thereof.

However, when air is introduced into the gas sensor 9 from air inlets 945 formed in a base end portion of the outer cover 942, water 7 may enter a clearance between the inner cover 941 and the outer cover 942 along a path, as indicated by a thick line W and accumulate, as clearly illustrated in FIG. 9, especially in a clearance 96 near the crimped portions 943, which will lead to the corrosion of an interface 8 between the inner cover 941 and the outer cover 942. Specifically, when the water 7 accumulates in the clearance 96, it results in a variation in concentration of oxygen between the clearance 96 and the interface 8 to facilitate or promote the transfer of metal ions from the inner and outer covers 941 and 942, thereby causing the interface 8 to be eroded.

SUMMARY OF THE INVENTION

It is therefore a principal object of the invention to avoid the disadvantages of the prior art.

It is another object of the invention to provide an improved structure of a gas sensor designed to minimize gap corrosion between an inner cover and an outer cover of an air cover assembly.

According to one aspect of the invention, there is provided a gas sensor which may be employed in measuring the concentration of a component of exhaust gasses emitted from automotive engines. The gas sensor comprises: (a) a sensor element sensitive to a gas to produce a signal as a function of concentration of the gas, the sensor element having a length with a top end and a base end opposite the top end; (b) a housing in which the sensor element is retained, the housing having a top end and a base end opposite the top end; (c) an air cover assembly having a top end and a base end opposite the top end, the air cover assembly being made up of an inner cover and an outer cover, the inner cover being secured to the base end of the housing, the outer cover surrounding the inner cover and being joined to the inner cover through at least one crimped portion; (d) an air inlet formed in a portion of the air cover assembly which is closer to the base end of the air cover assembly than the crimped portion, the air inlet being designed to admit air into the air cover assembly; and (e) an air chamber defined by the crimped portion between the inner and outer covers of the air cover assembly from the crimped portion circumferentially of the air cover assembly. The air chamber is exposed outside the air cover assembly at a side opposite the air inlet across the crimped portion to define a water drain path establishing fluid communication between the air inlet and outside the air cover assembly.

The crimped portion is formed to occupy only a portion of the circumference of the air cover assembly, thereby defining the air chamber in which the water drain path extends from the air inlet to outside the air cover assembly. When the water enters at the air inlet, it will flow between the inner and outer covers along the water drain path and drain out of the air cover assembly, thereby minimizing gap corrosion between the inner and outer covers of the air cover assembly.

According to another aspect of the invention, there is provided a gas sensor which comprises: (a) a sensor element sensitive to a gas to produce a signal as a function of concentration of the gas, the sensor element having a length with a top end and a base end opposite the top end; (b) a housing in which the sensor element is retained, the housing having a top end and a base end opposite the top end; (c) an air cover assembly having a top end and a base end opposite the top end, the air cover assembly being made up of an inner cover and an outer cover, the inner cover being secured to the base end of the housing, the outer cover surrounding the inner cover and being joined to the inner cover through a crimped portion which extends over the whole of a periphery of the air cover assembly; (d) an air inlet formed in a portion of the air cover assembly which is closer to the base end of the air cover assembly than the crimped portion, the air inlet being designed to admit air into the air cover assembly; and (e) a water drain hole formed in the air cover assembly to establish fluid communication of outside the air cover assembly with a clearance extending from the crimped portion to the air inlet between the inner and outer covers of the air cover assembly.

When the water enters at the air inlet, it will flow between the inner and outer covers and drain out of the air cover assembly from the water drain hole, thereby minimizing gap corrosion between the inner and outer covers of the air cover assembly.

In the preferred mode of the invention, the drain hole is formed in the outer cover of the air cover assembly to extend from an edge of the crimped portion toward the air inlet, thereby avoiding accumulation of the water around the crimped portion between the inner and outer covers to facilitate ease of draining of the water.

BRIEF DESCRIPTION OF THE DRAWINGS

The present invention will be understood more fully from the detailed description given hereinbelow and from the accompanying drawings of the preferred embodiments of the invention, which, however, should not be taken to limit the invention to the specific embodiments but are for the purpose of explanation and understanding only.

In the drawings.

DESCRIPTION OF THE PREFERRED EMBODIMENTS

Figure 1:
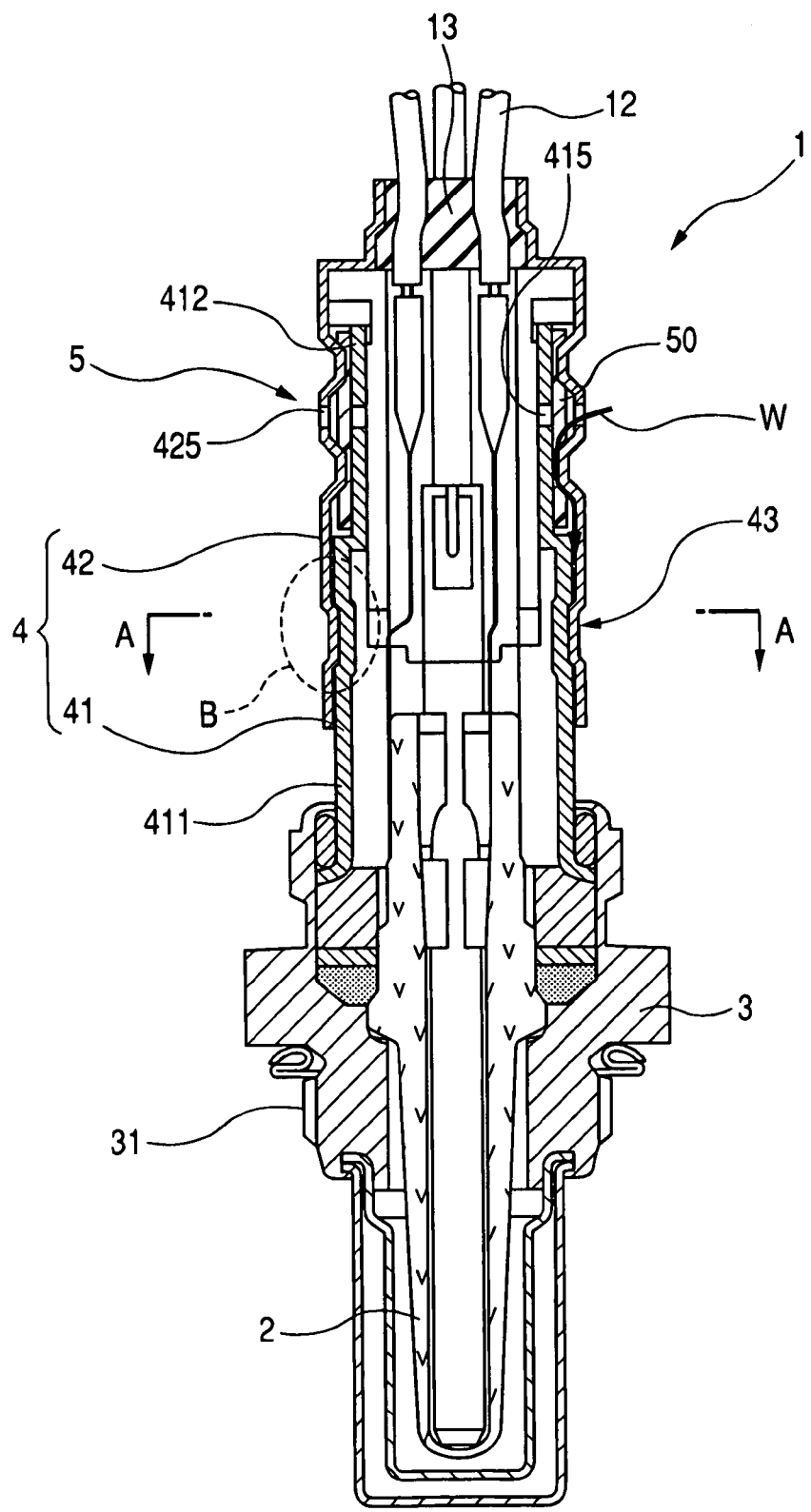
FIG. 1 is a longitudinal sectional view which shows an internal structure of a gas sensor according to the first embodiment of the invention.
Figure 2:
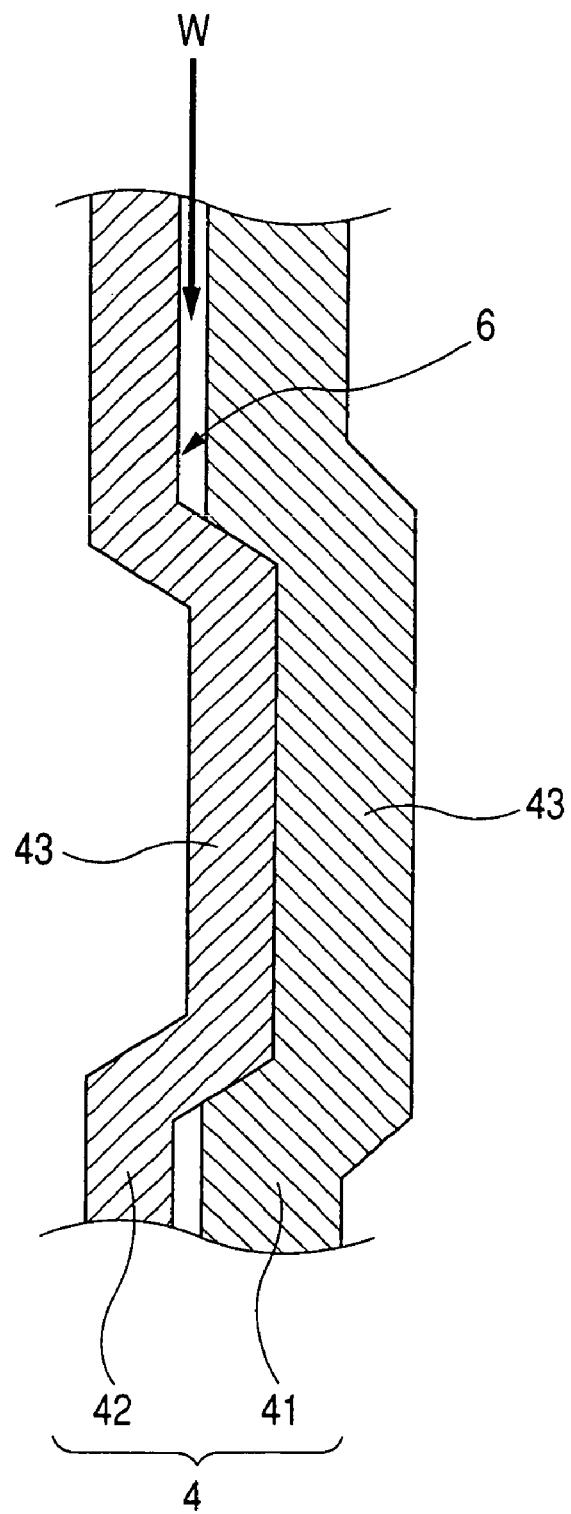
FIG. 2 is a partially enlarged sectional view, as circled by a broken line B in FIG. 1, which shows an inner and an outer cover of an air cover assembly of the gas sensor, as illustrated in FIG. 1.
Figure 3:
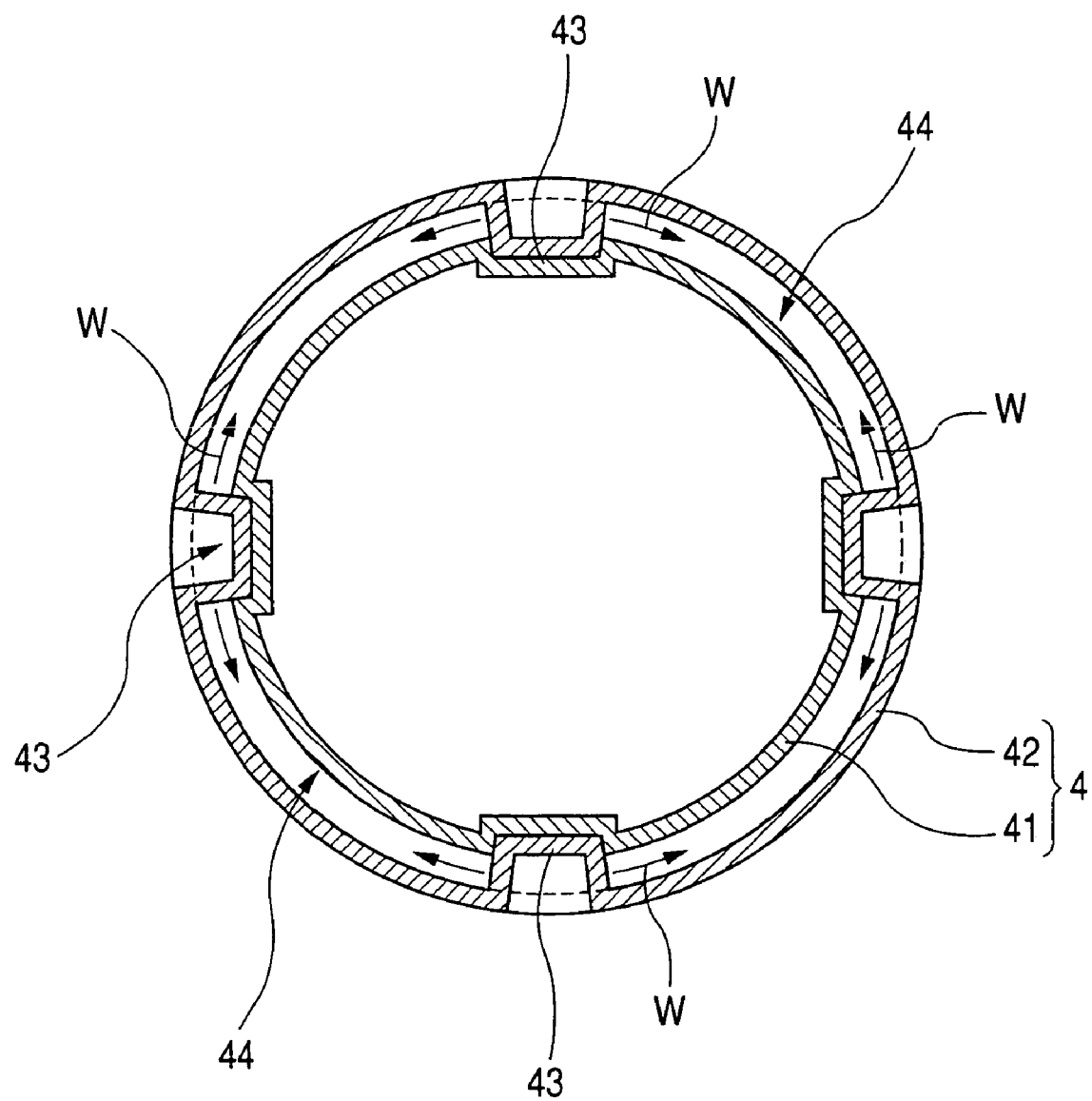
FIG. 3 is a transverse sectional view, as taken along the line A-A in FIG. 1.

Referring to the drawings, wherein like reference numbers refer to like parts in several views, particularly to FIGS. 1, 2, and 3, there is shown a gas sensor 1 according to the first embodiment of the invention which may be used in measuring the concentration of a given component of exhaust emissions of automotive engines. For instance, the gas sensor 1 may be designed as an $O_2$ sensor, an A/F sensor, or a NOx sensor.

The gas sensor 1 consists essentially of a sensor element 2 sensitive to a gas to be measured (which will also be referred to as a measurement gas below) to produce an electrical signal as a function of the concentration of the measurement gas, a housing 3 in which the sensor element 2 is retained, and an air cover assembly 4 joined to a base end (i.e., an upper end, as viewed in FIG. 1) of the housing 3.

The air cover assembly 4 is made up of an inner cover 41 and an outer cover 42. The inner cover 41 is secured at an end thereof to the base end of the housing 3. The outer cover 42 is placed to surround a base end portion (i.e., an upper end portion, as viewed in FIG. 1) of the inner cover 41.

The air cover assembly 4 has formed therein air inlets 5 through which air is admitted inside the gas sensor 1.

The air cover assembly 4 has, as clearly shown in FIGS. 1 and 3, joints 43 by which the inner and outer covers 41 and 42 are connected together. The joints 43 are, as can be seen in FIG. 1, located closer to the top (i.e., a lower end, as viewed in the drawing) of the gas sensor 1 than the air inlets 5 and formed by elastically deforming or crimping, for example, four circumferentially spaced portions of each of the inner and outer covers 41 and 42 inwardly. The joints 43 will also be referred to as crimped portions below. The crimped portions 43 define, as clearly illustrated in FIG. 3, air chambers 44 between adjacent two joints thereof which open outside the air cover assembly 4 at the top end of the outer cover 42.

The sensor element 2 is, as clearly shown in FIG. 1, of a cup-shape with a bottom.

The housing 3 has formed in an outer periphery thereof a thread 31 for installation of the gas sensor 1 in, for example, an exhaust pipe (not shown) of the automotive engine. When the gas sensor 1 is installed in the exhaust pipe, the top end portion (i.e. the lower end portion, as viewed in FIG. 1) of the gas sensor 1 extends downward within the exhaust pipe, while the base end portion (i.e., the upper end portion) of the gas sensor 1 extends upward outside the exhaust pipe.

The outer cover 42 has formed in the base end portion thereof air intake openings 425 through which the air is to be admitted thereinto.

The inner cover 41 is made up of a large-diameter portion 411 extending to the top end thereof and a small-diameter portion 412 extending to the base end thereof. The inner cover 41 has formed in the small-diameter portion 412 air intake holes 415 which face the air intake openings 425 radially of the air cover assembly 4.

The air cover assembly 4 also has a ventilation filter 50 made of, for example, a water-repellent filter 50 nipped between the inner cover 41 and the outer cover 42. The ventilation filter 50 constitutes the air inlets 5 along with the air intake openings 425 and the air intake holes 415.

The air cover assembly 4, as described above, has the four crimped portions 43 which are located at equi-intervals in the circumferential direction thereof to define the four air chambers 44, as clearly illustrated in FIG. 3, which are identical in size or volume with each other.

A rubber bush 13 is, as illustrated in FIG. 1, fitted in the base end of the air cover assembly 4. The rubber bush 13 retains therein leads 12 which are connected electrically with the sensor element 2 and is held by crimping the outer cover 42 inwardly to establish a liquid-tight seal in the base end of the gas sensor 1.

The gas sensor 1 is designed to have a drain path for water entering at the air inlets 5, as described below.

When the vehicle is splashed with water during traveling or washing, water may enter, as indicated by an arrow W, between the inner cover 41 and the outer cover 42 from the air inlets 5. The water then flows, as illustrated in FIG. 2, toward the top end or downward of the gas sensor 1, enters the air chambers 44, and drains outside the air cover assembly 4. When hitting one of the crimped portions 43, the water, as indicated by arrows W in FIG. 3, flows into an adjacent one(s) of the air chambers 44 and then drains outside the air cover assembly 4. This avoids the accumulation of the water between the inner cover 41 and the outer cover 42, thus preventing the gap corrosion therebetween.

The number of the crimped portions 43 is not limited to four. The air cover assembly 4 may alternatively have at least one crimped portion 43 to join the inner cover 41 and the outer cover 42 together.

Figure 4:
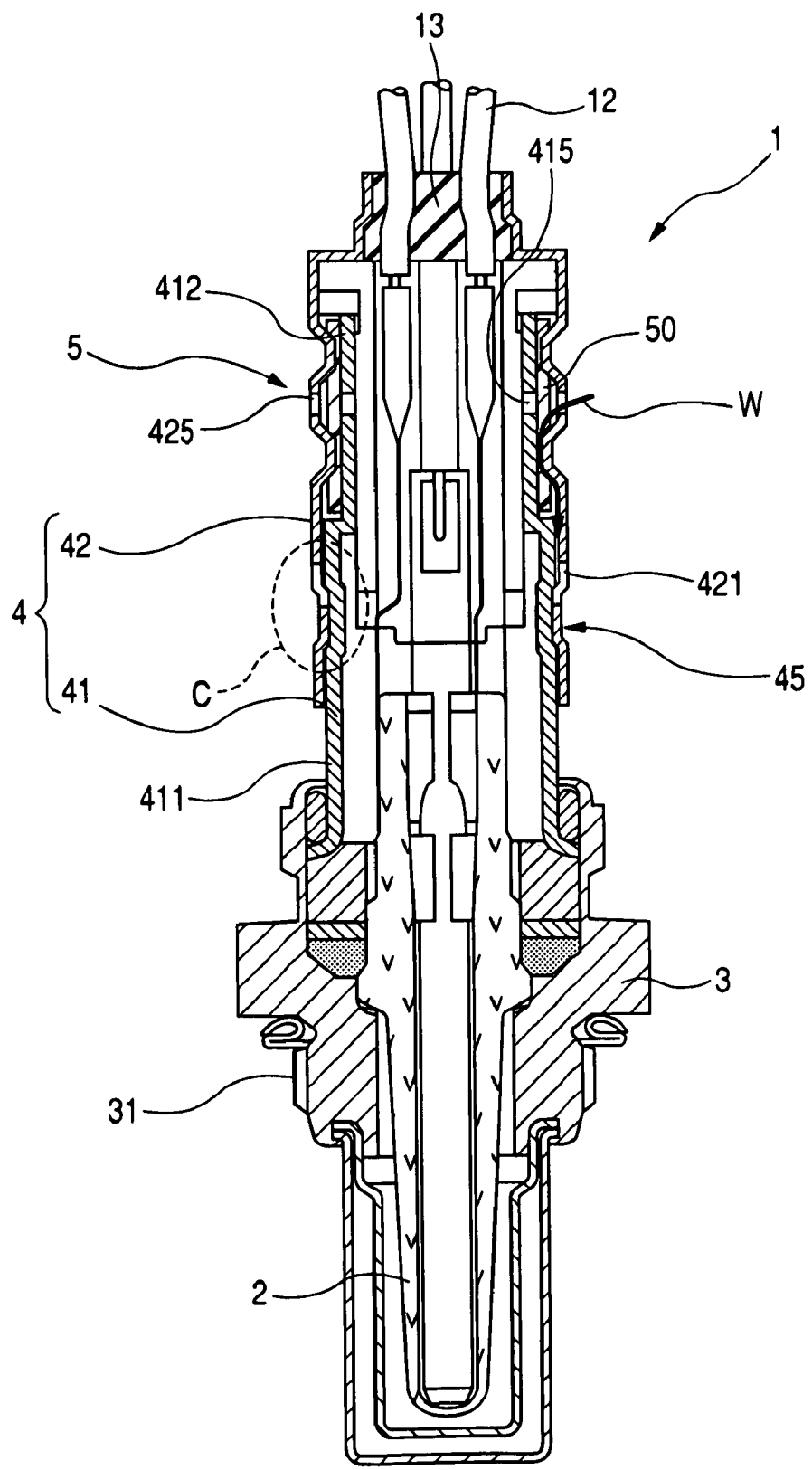
FIG. 4 is a longitudinal sectional view which shows an internal structure of a gas sensor according to the second embodiment of the invention.
Figure 5:
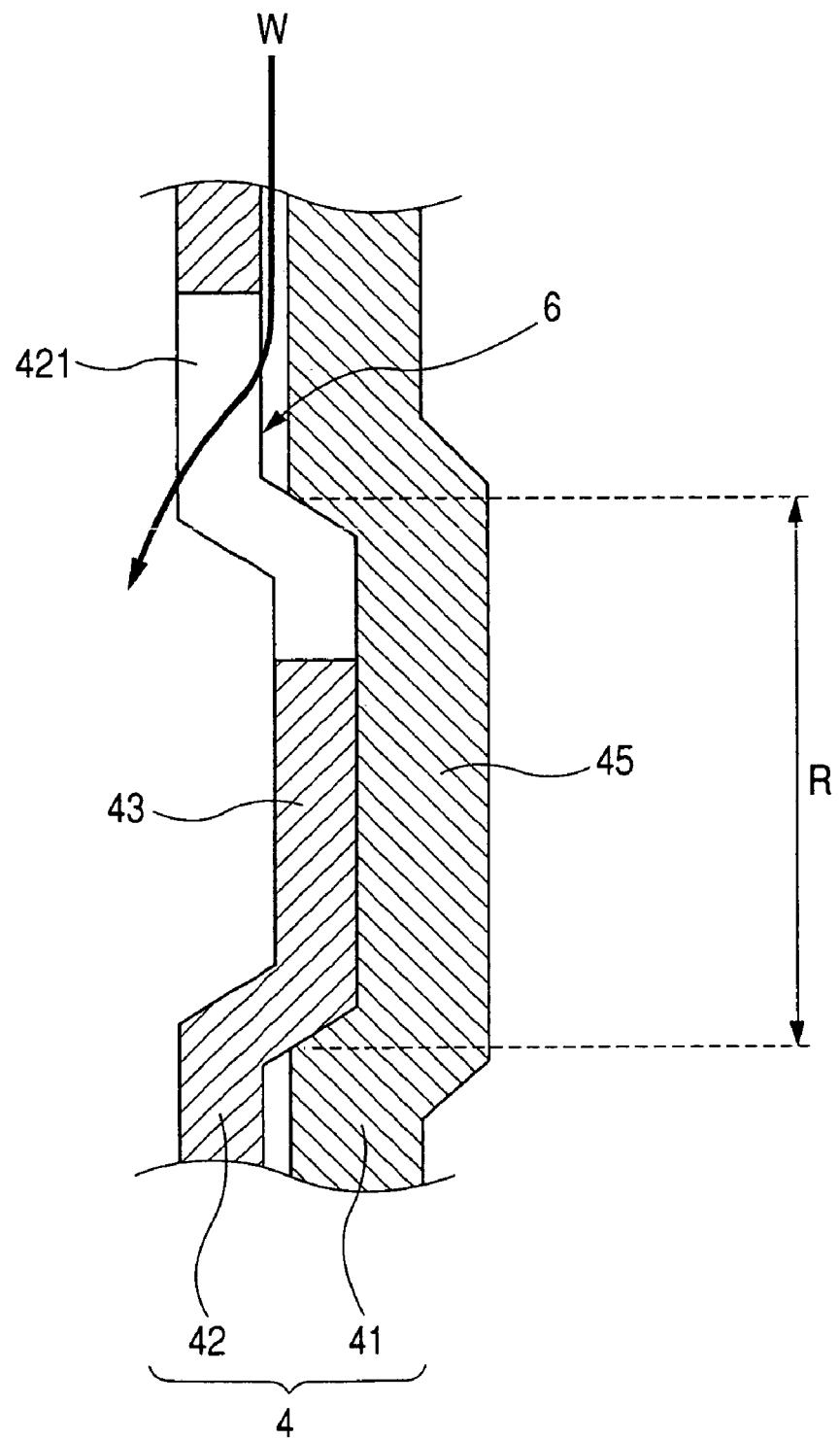
FIG. 5 is a partially enlarged sectional view, as circled by a broken line C in FIG. 4, which shows an inner and an outer cover of an air cover assembly of the gas sensor, as illustrated in FIG. 4.
Figure 6:
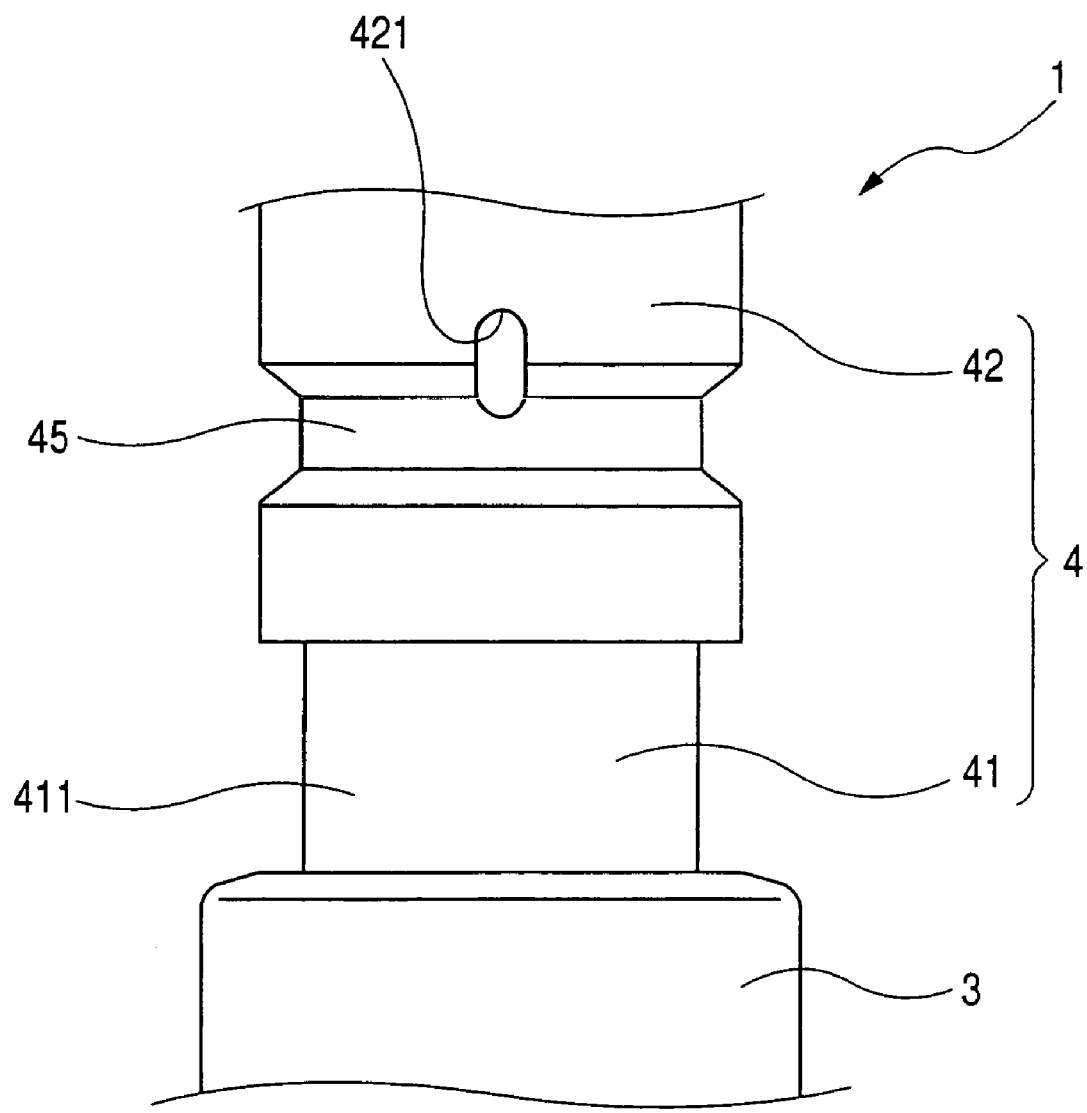
FIG. 6 is a partially side view which shows an air cover assembly of the gas sensor of FIG. 4.

FIGS. 4 to 6 show the gas sensor 1 according to the second embodiment of the invention which is different from the first embodiment in that the air cover assembly 4 has one crimped portion 45 which extends over the overall circumference of the air cover assembly 4 to join the inner and outer covers 41 and 42. The crimped portion 45 is, like the first embodiment, located closer to the top end of the gas sensor 1 than the air inlets 5.

The outer cover 42 has at least one drain hole 421 which is, as clearly illustrated in FIG. 6, formed to extend vertically across an upper edge of the crimped portion 45 closer to the base end of the air cover assembly 4. The water having flowed to the crimped portion 45 between the inner and outer covers 41 and 42 escapes, as indicated by an arrow W in FIG. 5, outside the air cover assembly 4 from the drain hole 421.

The crimped portion 45 of the air cover assembly 4, as referred to herein, is made up of portions of the inner and outer covers 41 and 42 which are, as illustrated in FIG. 5, pressed inwardly into direct abutment with each other in a range R.

Other arrangements are identical with those in the first embodiment, and explanation thereof in detail will be omitted here.

The inventor of this application performed corrosion tests in comparison of the gas sensor 1 with a conventional type of gas sensor.

The inventor prepared two types of test samples: one is the gas sensor 1 of the invention, and the other is a conventional type. Specifically, the inventor prepared, as can be seen from a graph of FIG. 7, four No. 1 test samples identical in structure with the one illustrated in FIG. 8 and sixteen No. 2 test samples identical in structure with the gas sensor 1, and broken down the No. 2 test samples into four groups.

Each of the corrosion tests was performed by installing one of the test samples in a pipe by screwing a thread (like the one, as denoted at 31 in FIG. 1) thereinto, heating the pipe for eighteen minutes until the thread reaches 300° C., and then spraying salt water containing 5% by weight of salt over the whole of a portion of the test sample exposed outside the pipe. This cycle was repeated 300 times for the No. 1 test samples and the first group of the No. 2 tests samples, 600 times for the second group of the No. 2 test samples, 900 times for the third group of the No. 2 test samples, and 1200 times for the fourth group of the No. 2 test samples.

The air cover assembly of each of the test samples is made of stainless steel (SUS304).

After the above corrosion tests, the inventor disassembled the air cover assembly of each of the test samples, removed extraneous matter from opposed surfaces of the inner and outer covers of the air cover assembly, and observed the surfaces visually using a microscope to check them for cracks. When the crack was found in either of the surfaces of the inner and outer covers, it was decided that the surfaces of the inner and outer covers were corroded. This is because usually, when corrosion occurs between the inner and outer covers, it will cause the opposed surfaces of the inner and outer covers to darken, but however, it is difficult to determine whether such darkening has arisen from corrosion or stains on the surfaces. Therefore, when the crack arising from the corrosion was visually perceived, corrosion was determined as having occurred between the inner and outer covers.

Figure 7:
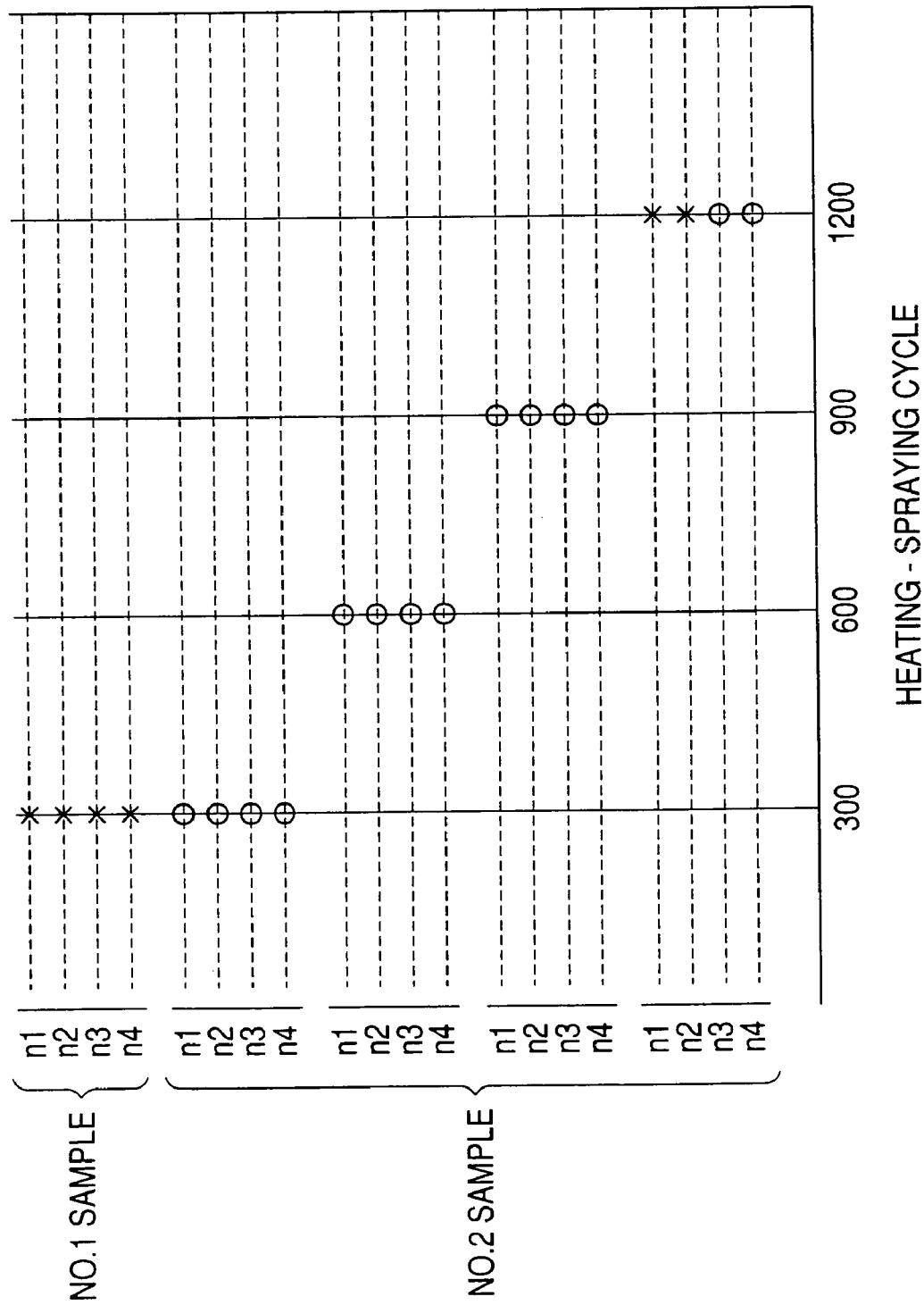
FIG. 7 is a graph which shows results of corrosion tests.
Figure 8:
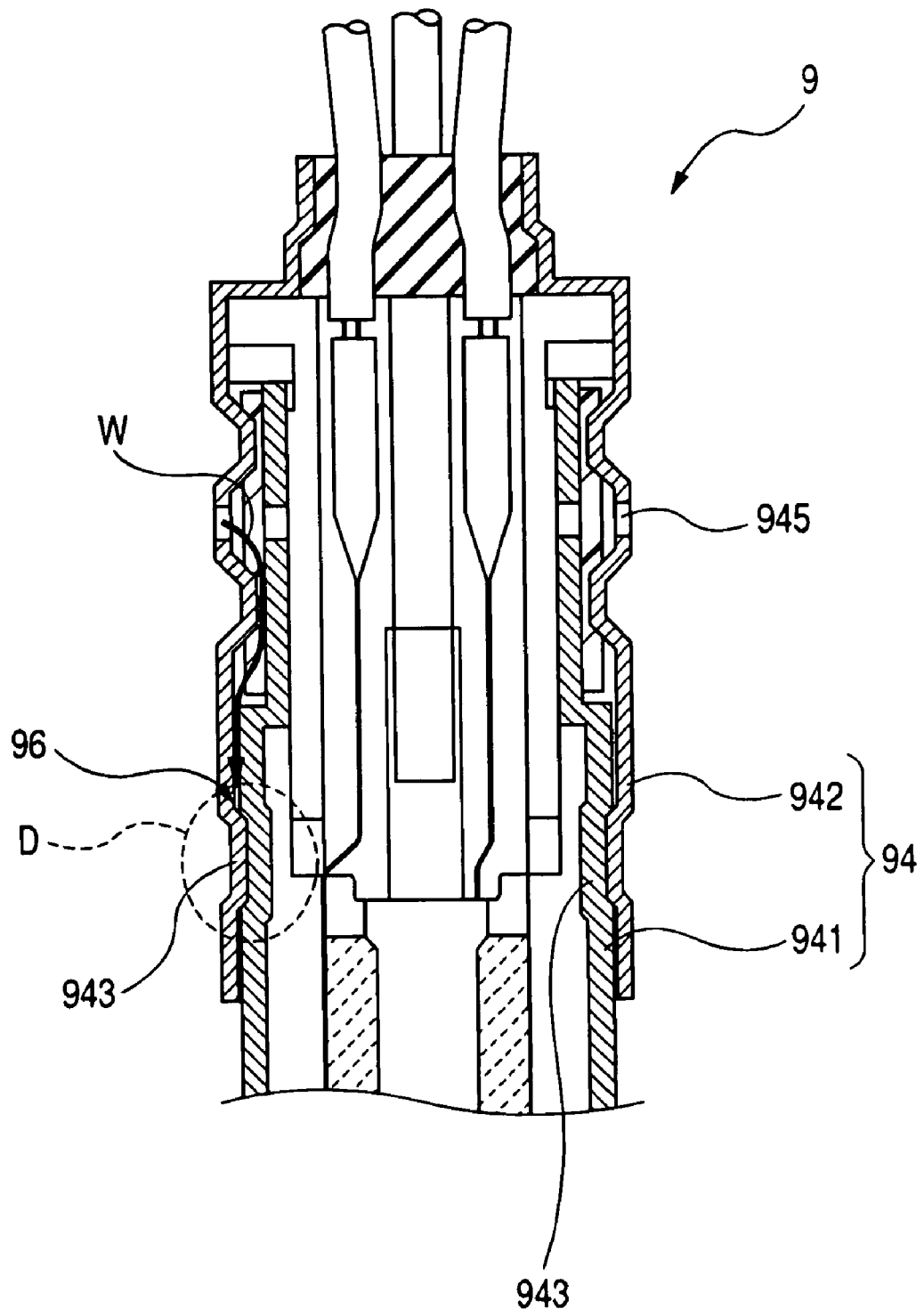
FIG. 8 is a partially longitudinal sectional view which shows an internal structure of a conventional gas sensor.
Figure 9:
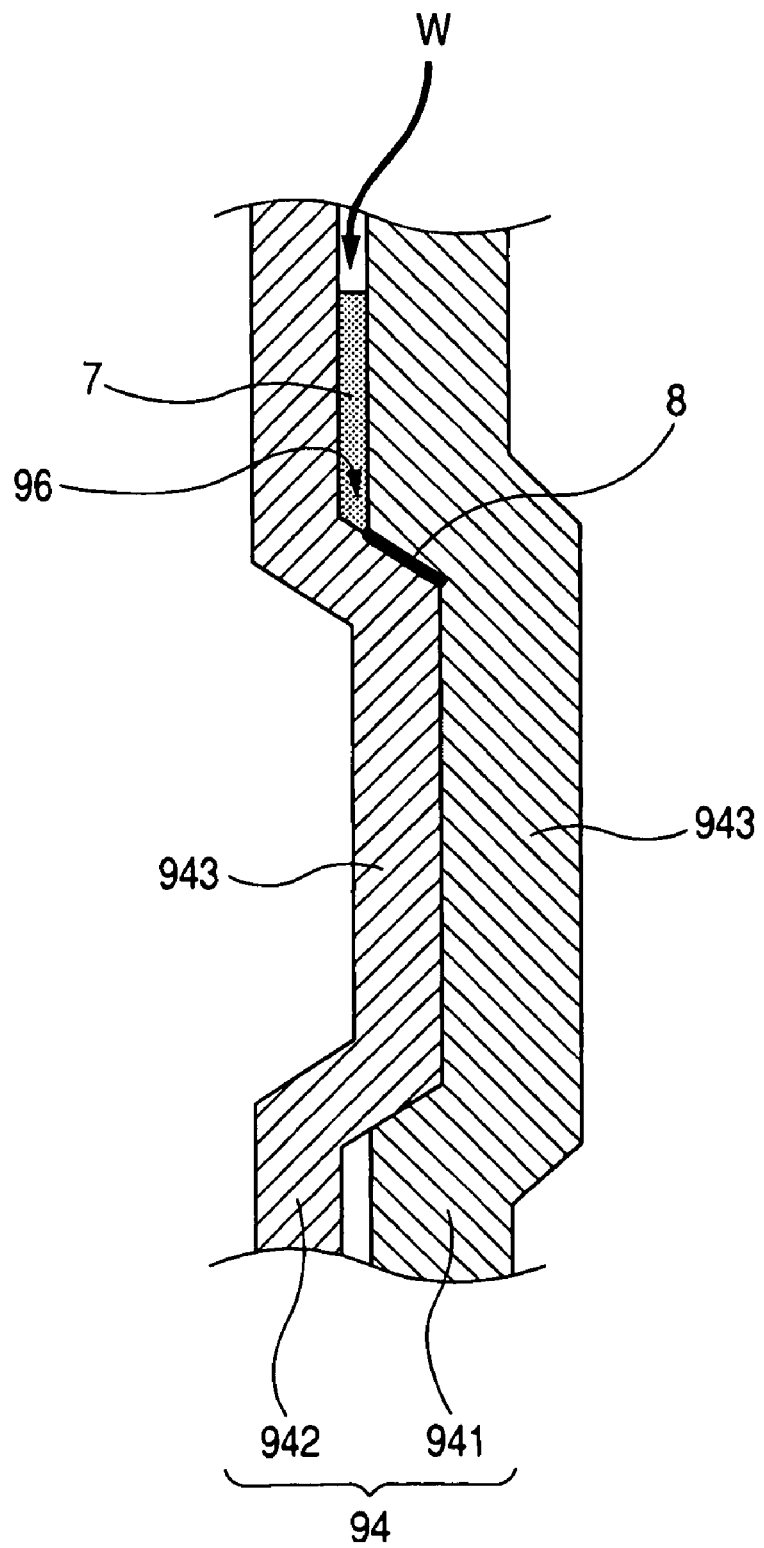
FIG. 9 is a partially enlarged sectional view, as circled by a broken line D in FIG. 8, which shows an inner and an outer cover of an air cover assembly of the gas sensor, as illustrated in FIG. 8.

Results of the corrosion tests are plotted in the graph of FIG. 7. The graph shows that when subjected to 300 cycles (100 hours) of the corrosion test, all the No. 1 test samples are cracked, and when subjected to 900 cycles (300 hours) of the corrosion test, the No. 2 test samples are all not yet cracked, however, when subjected to 1200 cycles (400 hours) of the corrosion test, two of the fourth group of the No. 2 test samples are cracked. It is, therefore, found that the structure of the gas sensor 1 is useful for avoiding corrosion between the inner and outer covers 41 and 42 of the air cover assembly 4 which usually leads to cracks.

While the present invention has been disclosed in terms of the preferred embodiments in order to facilitate better understanding thereof, it should be appreciated that the invention can be embodied in various ways without departing from the principle of the invention. Therefore, the invention should be understood to include all possible embodiments and modifications to the shown embodiments which can be embodied without departing from the principle of the invention as set forth in the appended claims.

What is claimed is:

1. A gas sensor comprising:
a sensor element sensitive to a gas to produce a signal as a function of concentration of the gas, said sensor element having a length with a top end and a base end opposite the top end;
a housing in which said sensor element is retained, said housing having a top end and a base end opposite the top end;
an air cover assembly having a top end and a base end opposite the top end, said air cover assembly being made up of an inner cover and an outer cover, the inner cover being secured to the base end of said housing, the outer cover surrounding the inner cover and being joined to the inner cover through at least one crimped portion;
an air inlet formed in a portion of said air cover assembly which is closer to the base end of said air cover assembly than the crimped portion, the air inlet being designed to admit air into said air cover assembly; and
an air chamber defined by the crimped portion between the inner and outer covers of said air cover assembly from the crimped portion circumferentially of said air cover assembly, said air chamber being exposed outside said air cover assembly at a side opposite said air inlet across the crimped portion to define a water drain path establishing fluid communication between said air inlet and outside said air cover assembly.

2. A gas sensor comprising:
a sensor element sensitive to a gas to produce a signal as a function of concentration of the gas, said sensor element having a length with a top end and a base end opposite the top end;
a housing in which said sensor element is retained, said housing having a top end and a base end opposite the top end;
an air cover assembly having a top end and a base end opposite the top end, said air cover assembly being made up of an inner cover and an outer cover, the inner cover being secured to the base end of said housing, the outer cover surrounding the inner cover and being joined to the inner cover through a crimped portion which extends over the whole of a periphery of said air cover assembly;
an air inlet formed in a portion of said air cover assembly which is closer to the base end of said air cover assembly than the crimped portion, the air inlet being designed to admit air into said air cover assembly; and
a water drain hole formed in said air cover assembly to establish fluid communication of outside said air cover assembly with a clearance extending from the crimped portion to said air inlet between the inner and outer covers of said air cover assembly.

3. A gas sensor as set forth in claim 2, wherein said drain hole is formed in the outer cover of said air cover assembly to extend from an edge of the crimped portion toward said air inlet.

* * * * *